(12) United States Patent
Ruff

(10) Patent No.: US 6,190,079 B1
(45) Date of Patent: Feb. 20, 2001

(54) SCRUBBING SOAP BAR

(76) Inventor: Patricia E. Ruff, 5939 St. Laurent Dr., Agoura Hills, CA (US) 91301

(*) Notice: Under 35 U.S.C. 154(b), the term of this patent shall be extended for 0 days.

(21) Appl. No.: 09/546,202

(22) Filed: Apr. 10, 2000

(51) Int. Cl.[7] .................................................. A47K 5/05
(52) U.S. Cl. ............................. 401/201; 401/8; 401/88; 510/146; D28/8.1
(58) Field of Search ....................... 401/201, 6–8, 401/49, 52, 88; D28/8.1, 8.2; 510/447, 143, 144, 146

(56) References Cited

U.S. PATENT DOCUMENTS

| | | |
|---|---|---|
| D. 375,383 | 11/1996 | Williams ............... D28/8.1 |
| D. 379,249 | 5/1997 | Williams ............... D28/8.1 |
| 389,296 | 9/1888 | Greeley . |
| 488,393 | 12/1892 | Jewett . |
| 821,245 | 5/1906 | Hutchinson . |
| 1,200,883 | 10/1916 | Scheufler et al. . |
| 1,351,311 | 8/1920 | Virneburg . |
| 1,416,962 | 5/1922 | Meeks . |
| 1,786,513 | 12/1930 | Zuckerman . |
| 1,787,660 * | 1/1931 | Blakeley ..................... 401/8 |
| 2,083,871 | 6/1937 | Serewicz .................... 15/122 |
| 2,160,921 | 6/1939 | Stroop ......................... 51/186 |
| 2,243,634 | 5/1941 | Kadish .......................... 45/28 |
| 2,883,791 * | 4/1959 | Ballo ............................ 401/8 |
| 3,196,112 | 7/1965 | Presley ........................ 252/92 |
| 3,341,457 | 9/1967 | Schmidt ....................... 252/92 |
| 3,488,126 * | 1/1970 | Avallone .................... 401/201 |
| 3,519,568 | 7/1970 | Needleman .................. 252/93 |
| 4,062,792 | 12/1977 | McNabb ...................... 252/93 |
| 4,190,550 | 2/1980 | Campbell ..................... 252/93 |
| 4,196,490 * | 4/1980 | Jonzon .......................... 401/8 |
| 4,228,834 | 10/1980 | Desnick ....................... 150/3 |
| 4,696,068 | 9/1987 | Kenner ........................ 4/606 |
| 4,741,852 | 5/1988 | Oudracek .................... 252/92 |
| 5,390,971 | 2/1995 | Warren ........................ 294/25 |
| 5,462,378 | 10/1995 | Webb ......................... 401/201 |
| 5,486,064 | 1/1996 | Schulte ...................... 401/201 |
| 5,545,456 | 8/1996 | Suida .......................... 428/76 |
| 5,704,723 | 1/1998 | Salisian ........................ 401/8 |
| 5,857,792 | 1/1999 | Iffinger ........................ 401/19 |
| 5,895,163 | 4/1999 | Chapman .................... 401/201 |

* cited by examiner

*Primary Examiner*—Charles R. Eloshway
(74) *Attorney, Agent, or Firm*—Jack C. Munro

(57) ABSTRACT

A scrubbing soap bar that is composed of vegetable oil and glycerine within which is imbedded a length of a thin, fine mesh netting with a portion of the netting extending exteriorly of the soap bar. The portion of the netting that extends exteriorly of the soap bar forms a pocket which facilitates insertion of a human user's finger(s) which facilitates grasping and holding onto the soap bar as the soap bar is used.

2 Claims, 2 Drawing Sheets

SCRUBBING SOAP BAR

BACKGROUND OF THE INVENTION

1). Field of the Invention

The field of this invention relates to cleaning implements and more particularly to the construction of a soap bar which includes an imbedded scrubber.

2). Description of the Prior Art

Bar soap is in exceedingly common use by everybody throughout the world for personal bathing. Bars of soap are soluble in water. The composition of a bar of soap can vary greatly, but it is common for bars of soap to contain some type of an oil, such as a vegetable oil, and glycerine. Also, bars of soap can also contain water, moisturizers, emulsifiers, vitamins, perfumes and possibly dyes. A typical bar of soap also may contain numerous other ingredients. As the bar of soap is used, it decreases in volume until eventually a remaining small portion of the soap bar is discarded or is completely dissolved.

Because soap is a base, it has a slippery nature. The slippery nature makes it easy for the soap to slip from one's hand and be dropped. Dropping of a soap bar within a bathtub or shower is an exceedingly common occurrence. It can be difficult, even to people having the greatest dexterity, to pick up a dropped soap bar. It would be desirable to construct a soap bar in such a manner as to minimize the possibility of being dropped.

Additionally, in order to facilitate the removal of dead skin and also facilitate the cleaning of one's skin, it is common to utilize some form of a light scrubber when scrubbing of one's body. A common form of a scrubber is a washrag or a long strip of netting. In the past, wash rags and netting have been used separately in conjunction with a soap bar.

SUMMARY OF THE INVENTION

The soap bar of the present invention is designed to include a scrubber imbedded therein. The scrubber is constructed of a thin, fine mesh netting which is placed within a mold prior to pouring into the mold the composition of the soap bar. The netting is to include a center section which can be referred to as a strip. This strip is to be located exteriorly of the soap bar after the soap bar is completely poured. Between the surface of the soap bar and the netting there is formed a pocket, and within this pocket, a user's finger(s) can be inserted which facilitates grasping and holding onto the soap bar as it is used. The scrubber also applies a light abrasive action to the user's skin during usage of the soap bar which facilitates cleaning of one's skin and removing of dead skin. As the soap bar is consumed, more than likely there will occur additional pockets which can also be used to facilitate the retaining and holding onto the soap bar.

The primarily objective of the present invention is to construct a soap bar which includes an internal scrubber.

Another objective of the present invention is to construct a soap bar wherein the internal scrubber can be used as a device that facilitates holding onto and grasping of the soap bar as it is being used.

BRIEF DESCRIPTION OF THE DRAWINGS

For a better understanding of the present invention, reference is to be made to the accompanying drawings. It is to be understood that the present invention is not limited to the precise arrangement shown in the drawings.

DETAILED DESCRIPTION OF THE PREFERRED EMBODIMENT

Figure 1:
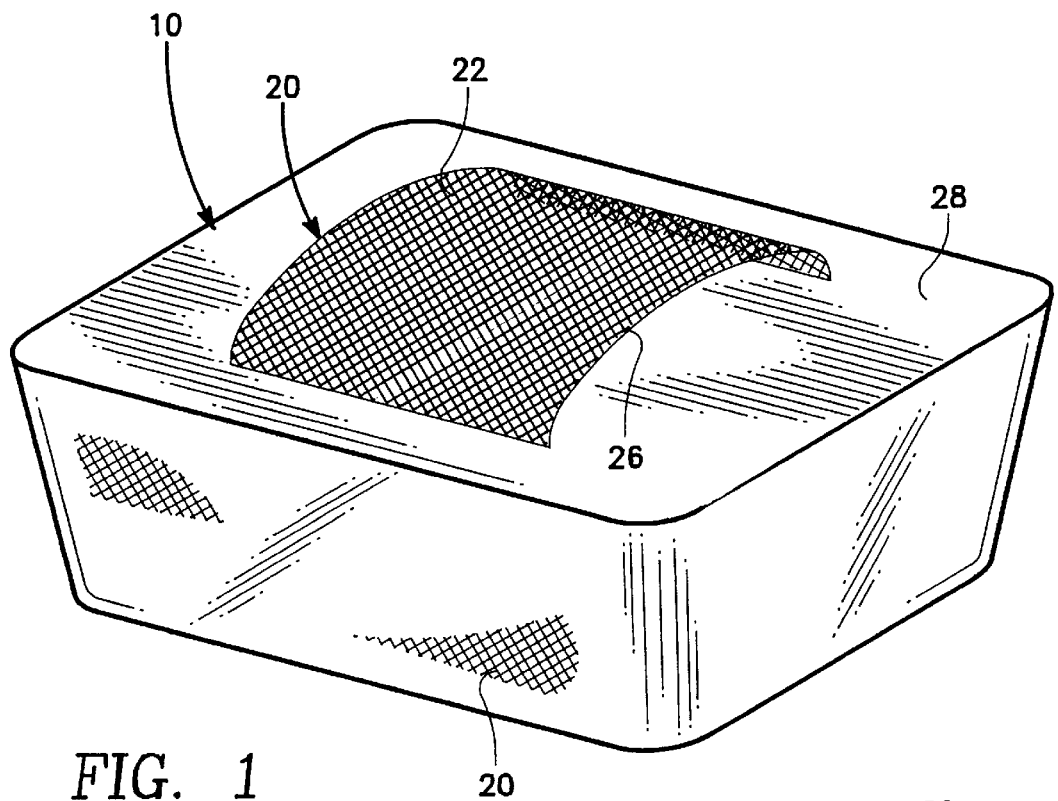
FIG. 1 is an isometric view of the soap bar constructed in accordance with this invention.
Figure 2:
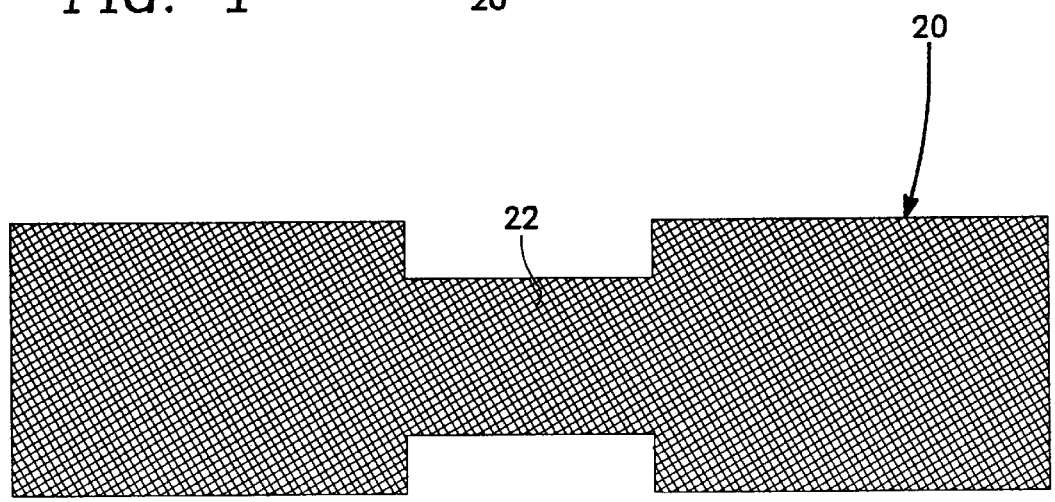
FIG. 2 is a top plan view of the scrubber located in its stretched configuration prior to being imbedded within the soap bar of FIG. 1.
Figure 3:
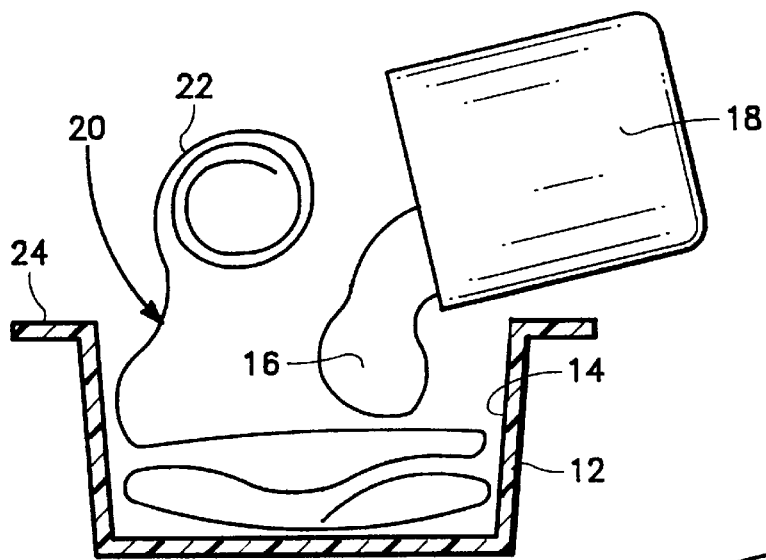
FIG. 3 is a view depicting forming of the soap bar of FIG. 1 within a mold with the scrubber being imbedded within the mold and the soap composition being shown in an initial stage of being poured into the mold.
Figure 4:
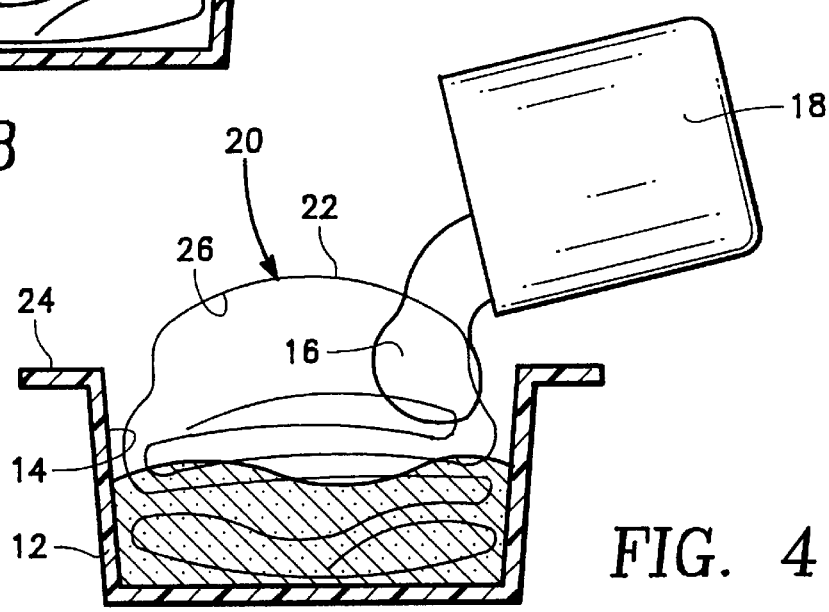
FIG. 4 is a view similar to FIG. 3 but showing the mold approximately half filled with the soap composition.
Figure 5:
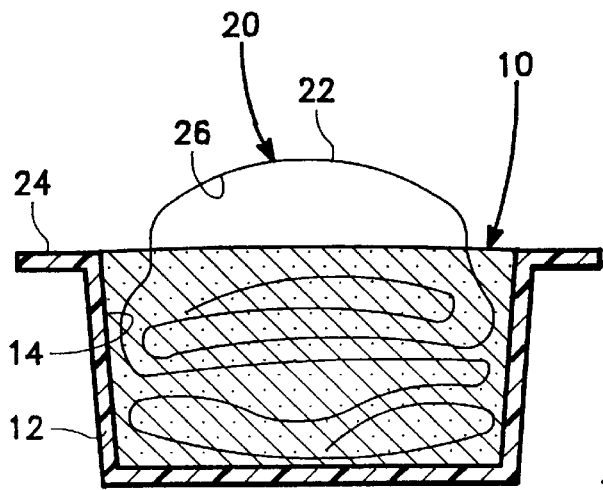
FIG. 5 is a view similar to FIG. 4 but with the mold in a completely filled state by the soap composition.

Referring particularly to the drawings, there is shown in FIG. 1 the soap bar 10 constructed in accordance with this invention. The soap bar is to be formed of one or more vegetable oils, such as coconut, peanut, castor and/or safflower and glycerine, water, aloe vera extract, moisturizers, emulsifiers and Vitamin E. Also, the composition of soap bar 10 will frequently include either a dye or a perfume. The soap bar 10 is constructed by utilizing of a mold 12 which has a cavity 14. It is to be understood that in normal operation, the mold 12 will have a plurality of the cavities 14 so that a plurality of the soap bars 10 can be made at the same time. The composition of soap is heated so it will become liquid with this liquid soap 16 to be poured from a container 18 to within the cavity 14. Prior to initiating of the pouring of the liquid soap 16 into the cavity 14, there is to be inserted within the cavity 14 a section 20 of a thin, fine mesh netting. A typical material of construction for the section 20 would be nylon. However, other materials could be utilized such as an acetate or rayon.

The section 20 is to include a narrowed center strip 22. The section 20 is to be wadded and placed within the mold 12 so that the center strip 22 will extend above the upper surface 24 of the mold 12. The result is that after the mold cavity 14 is completely filled with the composition of the soap 10 and hardens, and when the resultingly formed soap bar 10 is removed from the cavity 14, that there is formed a pocket 26 between the strip 22 and the surface 28 of the soap bar 10. Within this pocket 26 is to be locatable one or more fingers of the human user in order to facilitate picking up, grasping and maneuvering of the soap bar 10 during usage. Other portions of the section 20 will become exposed as the soap bar 10 is consumed with this section 20 to function as a lightly abrasive material against the user's skin which facilitates the removal of dead skin and the cleaning of the skin.

The inserting of the fine, mesh netting section 20 within the mold cavity 14 is to be accomplished in not a specific manner with the exception of making sure that the center strip 22 will end up located exteriorly of the surface 28 of the soap bar 10. As the soap bar 10 is consumed and is reduced in volume, there will inherently be exposed other sections of the section 20 which will also form pockets, which are not shown, which will facilitate grasping, holding and maneuvering of the soap bar 10 during usage. It is to be noted that the center strip 22 is narrowed relative to the remaining portion of the section 20 so that the section 20 will not extend the entire length of the soap bar 10. It is normally preferable that the center strip 22 be of a shorter length than the length of the soap bar 10 which facilitates the maneuvering of the soap bar 10 as it is used.

The present invention may be embodied in other specific forms without departing from the essential attributes thereof. Reference should be made to the appending claims rather than the foregoing specification as indicating the scope of the invention.

What is claimed is:

1. A scrubbing soap bar comprising:

a body composed of vegetable oil and glycerine, said body having a surface, said body having an initial state which is of maximum volume and a consuming state which is of a volume less than said maximum volume; and a section of thin, fine mesh netting wadded and imbedded within said body so as to be substantially distributed throughout said body when said body is in said initial state, at least one strip integral with said section extends exteriorly of said body, said strip defining a pocket located exteriorly of said surface, whereby said pocket permits insertion of at least one finger of a human user which assists in grasping onto and holding said body as said body is used by applying such to a user's skin and when said body is in said consuming state, said netting is gradually exposed at various locations about the body, each said location; functioning as a lightly abrasive scrubber against the user's skin and as a gripping portion for holding said body.

2. A method of making a scrubbing soap bar comprising the steps of:

utilizing a mold having a mold cavity;

obtaining a length of a fine mesh netting which terminates at ends;

wadding and placing of said netting within said mold cavity so a portion of said netting located between said ends protrudes exteriorly of said mold cavity with the majority of said netting remaining wadded within said mold cavity to be gradually exposed at various locations as the soap bar is consumed;

filling of said mold cavity with a composition of liquid soap with said portion protruding forming a pocket between said liquid soap and said netting;

causing said liquid soap to harden into a solid bar; and removing said bar from said mold cavity.

* * * * *